(12) United States Patent
Wong et al.

(10) Patent No.: US 8,967,161 B2
(45) Date of Patent: Mar. 3, 2015

(54) ELASTOMERIC DENTAL FLOSS

(75) Inventors: Chi Shing Wong, Warren, NJ (US); Jose Eder Fontana, Sao Paulo (BR); Paulo Focassio, Sao Paulo (BR)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/883,451

(22) PCT Filed: Nov. 5, 2010

(86) PCT No.: PCT/US2010/055667
§ 371 (c)(1),
(2), (4) Date: May 3, 2013

(87) PCT Pub. No.: WO2012/060843
PCT Pub. Date: May 10, 2012

(65) Prior Publication Data
US 2013/0228193 A1 Sep. 5, 2013

(51) Int. Cl.
*A61C 15/00* (2006.01)
*A61C 15/04* (2006.01)
*A61Q 11/00* (2006.01)
*A61K 8/90* (2006.01)
*A61K 8/02* (2006.01)

(52) U.S. Cl.
CPC .............. *A61C 15/041* (2013.01); *A61Q 11/00* (2013.01); *A61K 8/90* (2013.01); *A61K 8/0283* (2013.01)
USPC .......................................... 132/321

(58) Field of Classification Search
CPC ........................................................ A61C 15/04
USPC .................................... 132/321–329
See application file for complete search history.

(56) References Cited

U.S. PATENT DOCUMENTS

| | | |
|---|---|---|
| 5,334,646 A | 8/1994 | Chen |
| 5,508,334 A | 4/1996 | Chen |
| 5,755,243 A | 5/1998 | Roberts et al. |
| 5,875,797 A | 3/1999 | Chiang et al. |
| 5,918,609 A | 7/1999 | Tsao et al. |
| 5,941,256 A | 8/1999 | Guay et al. |
| 5,962,572 A | 10/1999 | Chen |
| 6,029,678 A | 2/2000 | Tsao et al. |
| 6,161,555 A | 12/2000 | Chen |
| 6,333,374 B1 | 12/2001 | Chen |
| 6,340,027 B1 | 1/2002 | Hagne et al. |
| 2004/0123877 A1 | 7/2004 | Brown et al. |

FOREIGN PATENT DOCUMENTS

| | | |
|---|---|---|
| TW | 200946083 | 11/2009 |
| WO | WO 2011/057095 | 5/2011 |

OTHER PUBLICATIONS

International Search Report and Written Opinion in International Application No. PCT/US10/055667, mailed Aug. 1, 2011.
Written Opinion in International Application No. PCT/US10/055667, mailed Dec. 7, 2012.

*Primary Examiner* — Rachel Steitz
(74) *Attorney, Agent, or Firm* — Anne Louise St. Martin

(57) ABSTRACT

Described herein are dental floss compositions comprising an elastomeric matrix containing one or more particles, and methods of making and using the same.

19 Claims, 1 Drawing Sheet

ELASTOMERIC DENTAL FLOSS

BACKGROUND

The use of dental floss and other interdental cleaners are an important part of dental hygiene, and are used to remove plaque and other particulate from between the teeth and under the gum line, e.g., areas in the mouth where a toothbrush cannot reach. Frequently, these are the initiation sites of tooth decay, especially if not cleaned regularly. However, even with routine maintenance, caries and gingivitis still develop in these areas. Thus, there is a continuing need to develop more effective dental flosses.

Dental flosses are generally linear strips of a material having a fixed diameter and fixed dimensions. However, teeth are not all equally spaced apart. Thus, use of a dental floss that has a diameter less than the distance between the teeth results in inefficient or ineffective cleaning between the teeth. In addition, a space usually resides between the gum and two adjacent teeth that is usually larger than the diameter of dental floss, and efficient cleaning of such area is difficult. Dental floss users occasionally use dental floss to massage the gums, but dental flosses generally are hard when pulled taut, resulting in potential damage to the gum.

Solutions to overcome such problems include manufacturing dental flosses having a wider diameter. This may pose problems insofar as it may be difficult to pass larger diameter flosses, or even normal diameter flosses, between the teeth without a substantial increase of force. The force exerted to pass the floss between the teeth is immediately released once the floss passes between the teeth, usually resulting in a painful collision with the gums, and resulting in possible lacerations and bleeding. Also this "extra" force exerted to pass the floss between the teeth can cause the floss to shred and fray. Thus, small children may even be discouraged from flossing due to possible self-inflicted injuries.

Gelatinous elastomeric articles are known in the art, and often are used as handles for umbrellas, brushes, or for toys, dental floss, hand exercising grips, cushions, and the like. U.S. Pat. Nos. 5,334,646, and 5,508,334, the disclosures of which are incorporated by reference herein in their entirety, discloses a gelatinous composition comprised of an intimate blend admixture of poly(styrene-ethylene-butylene-styrene) triblock copolymer with a high level of a plasticizing oil. These gelatinous polymers usually are too jelly-like and lack sufficient rigidity to be used in dental floss applications, because, inter alia, they tend to break too easily upon elongation (i.e., the tensile strength at break is too high, and the elongation at break is too low for practical use). U.S. Pat. No. 5,962,572, the disclosure of which is incorporated by reference herein in its entirety, discloses oriented gels useful in a variety of applications such as low frequency vibration applications, damping of mechanical structures, and the like.

U.S. Pat. No. 5,755,243, the disclosure of which is incorporated by reference herein in its entirety, discloses a dental floss comprised of a fiber core, surrounded by an elastomeric outer layer. The outer layer provides a softer coating on a thicker floss used as a brush portion of a floss, but the floss itself is not stretchable due to the inner fiber core. A similar floss is disclosed in U.S. Pat. No. 5,875,797, the disclosure of which is incorporated by reference herein in its entirety. U.S. Pat. No. 5,918,609, the disclosure of which is incorporated by reference herein in its entirety discloses particulate modified elastomeric flosses in which particulate modification agents are either adsorbed to the surface of the floss or embedded in the surface of the floss.

U.S. Pat. No. 5,941,256, the disclosure of which is incorporated by reference herein in its entirety, discloses a dental floss having microcapsules associated with a portion of the floss that will burst and release a color to indicate use of the floss. U.S. Pat. No. 6,029,678, the disclosure of which is incorporated by reference herein in its entirety, discloses a "gel" dental floss that comprises a core material and a gel material in which the core material provides for sufficient tensile strength and the gel component provides for softness of the floss. U.S. Pat. No. 6,161,555, the disclosure of which is incorporated by reference herein in its entirety, discloses a dental floss in the form of a strand or tape made from gels having improved high tear strength and improved high tensile strength.

Despite the foregoing developments, there remains a need to develop dental floss compositions that solve such problems.

SUMMARY

Accordingly, some embodiments of the present invention provide a dental floss comprising an elastomeric matrix containing one or more particles, wherein the dental floss is adapted such that at least one of said one or more particles protrude from the matrix in increasing amounts as increasing tensile stress is applied to the dental floss.

In certain embodiments, the elastomeric matrix comprises: (a) a blend of an elastomeric block copolymer and polypropylene; and (b) a plasticizer.

In certain embodiments, the dental floss is provided by a process wherein the elastomeric block copolymer, the polypropylene, the plasticizer and at least one of the one or more particles are mixed and subsequently extruded or injected.

In certain embodiments, the elastomeric block copolymer comprises a styrene-ethylene/butylene-styrene block copolymer.

In certain embodiments, the elastomeric block copolymer comprises 50% to 99% by weight of the blend.

In certain embodiments, the polypropylene comprises 1% to 50% by weight of the blend.

In certain embodiments, the blend comprises 30% to 99% by weight of the dental floss.

In certain embodiments, the styrene-ethylene/butylene-styrene block copolymer comprises 20% to 40% by weight of styrene.

In certain embodiments, the plasticizer is a mineral oil, naphthenic oil, or a combination thereof.

In certain embodiments, the dental floss further comprises a flavorant, a colorant, a fluoride ion source, an antiseptic or antimicrobial agent, an analgesic agent, an anti-inflammatory agent, a coagulant, a vitamin, and a combination of two or more thereof.

In certain embodiments, the dental floss is adapted to withstand being elongated up to 1500% of an initial length without breaking.

In certain embodiments, the dental floss has a tensile strength peak at breaking point, for a 2 mm wide sample, as measured on an Instron 4464 with $2.76 \times 10^5$ Pa (40 psig) grips, of less than 20 N·min or less than 18 N·min.

In certain embodiments, the dental floss has an elongation at breaking point, for a 2 mm wide sample, as measured on an Instron 4464 with $2.76 \times 10^5$ Pa (40 psig) grips, of more than 100% or more than 200%.

In certain embodiments, the dental floss has a maximum elongation before breaking, for a 2 mm wide sample, as measured on an Instron 4464 with 2.76×105 Pa (40 psig) grips, of less than 0.35 mm.

In certain embodiments, the one or more particles are present in an amount greater than 2% by weight based on a weight of the dental floss.

In certain embodiments, the one or more particles have an average diameter of greater than 300 microns. In some embodiments, the one or more particles have an average diameter of about 350 microns.

In certain embodiments, the floss has a particle density of 0.1-100 particles/mm$^3$.

In certain embodiments, at least one of the one or more particles is an abrasive particle selected from the group consisting of silica, precipitated calcium carbonate, di-calcium phosphate, mica, crystalline alumino-silicate, precipitated silica, glass beads, glass bubbles, glass microspheres, ceramic microspheres and polymers having a melting point above 200° C.

In certain embodiments, a stretched nodule density for the dental floss stretched to twice a relaxed length is 0.1-100 particles/mm$^3$.

In certain embodiments, a stretched nodule density for the dental floss stretched to twice a relaxed length is at least 1.1× greater than a relaxed nodule density for the dental floss at the relaxed length.

BRIEF DESCRIPTION OF THE DRAWINGS

A more complete understanding of the present invention and the advantages thereof may be acquired by referring to the following description in consideration of the accompanying drawings, in which like reference numbers indicate like features.

DETAILED DESCRIPTION

Figure 1:
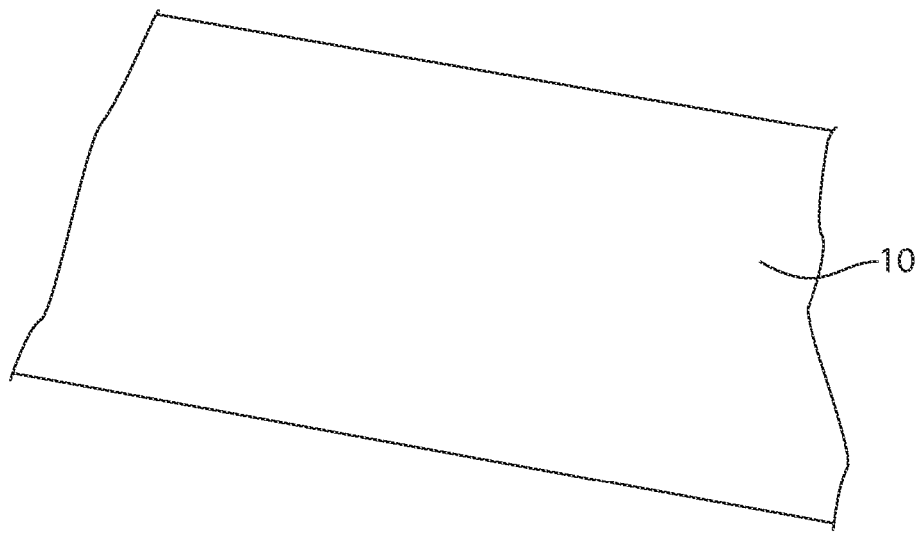
FIG. 1 depicts an embodiment of the inventive floss containing amorphous silica particles, wherein the floss is in a relaxed state.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. In addition, the compositions and the methods may comprise, consist essentially of, or consist of the elements described therein.

Unless otherwise specified, all percentages and amounts expressed herein and elsewhere in the specification should be understood to refer to percentages by weight. The amounts given are based on the active weight of the material. The recitation of a specific value herein is intended to denote that value, plus or minus a degree of variability to account for errors in measurements. For example, an amount of 10% may include 9.5% or 10.5%, given the degree of error in measurement that will be appreciated and understood by those having ordinary skill in the art.

In some embodiments, the inventive dental floss comprises at least one elastomeric material that can be enlarged and swelled without breaking in a normal flossing operation. In some embodiments, the dental floss provides improved and gentler application to the gums, is capable of massaging the gums, is more interesting and fun to use, and is flexible to allow easy handling during flossing.

In some embodiments, the elastomeric dental floss comprises at least an elastomeric block copolymer, polypropylene, a plasticizer, one or more abrasive particles, an optional flavorant, and an optional colorant. In some embodiments, the elastomeric dental floss preferably can be elongated up to 1,500% of its initial length without breaking, has a tensile strength peak at breaking point, for a 2 mm wide sample, as measured on an Instron 4464 with 2.76×10$^5$ Pa (40 psig) grips, of less than 20 N·min, and has an elongation at breaking point, for a 2 mm wide sample, as measured on an Instron 4464 with 2.76×10$^5$ Pa (40 psig) grips, of more than 100%.

In other embodiments, the elastomeric dental floss is prepared by extrusion or injection molding a mixture of at least an elastomeric block copolymer, polypropylene homopolymer, one or more abrasive particles, a mineral oil, an optional flavorant, and an optional colorant through a die to produce a filament dental floss product.

It was a surprising discovery that a gel composition may be effectively used as a dental floss. Generally, the gel composition comprises a blend of an elastomeric block copolymer, preferably a styrene-ethylene-butylene-styrene (SEBS) block copolymer, polypropylene homopolymer, and a plasticizer, and is a deformable and stretchable solid, that narrows as it is stretched. In some embodiments, the gel composition comprises a melted blend of an elastomeric block copolymer, preferably a styrene-ethylene-butylene-styrene (SEBS) block copolymer, polypropylene homopolymer, and a plasticizer, and is a deformable and stretchable solid, that narrows as it is stretched. The gel composition may be stretched up to 3000% of its original length, and return to within 100% to 120% of its original length when relaxed. Generally, the gel composition "narrows" as it becomes stretched, and "thickens" or returns to its original diameter when relaxed. In some embodiments, the gel composition may be stretched to be manipulated between teeth, and relaxed when contacting the gums, e.g., to clean the area.

In some embodiments, the dental floss is in the form of a solid gel composition, and may be produced by extrusion methods or injection molding methods known by persons having ordinary skill in the art into filaments that also exhibit a gel like consistency, e.g., are readily deformable and stretchable, but return to their original size and shape after such deformation and stretching. In some embodiments, the composition comprises an elastomeric polymeric material comprising from 80 to 99% by weight of an SEBS (styrene-ethylene/butylene-styrene) block copolymer having an unsaturated mid-block chain, from 1 to 20% by weight of a polypropylene homopolymer, from 0.01 to 5% by weight of a mineral oil. In some embodiments, the composition may further comprise from 0.001% to 1% by weight of a colorant, and/or from 0.05 to 1.5% of a flavorant.

Any suitable SEBS block copolymer can be used so long as it provides a final composition having the desired properties described herein. U.S. Pat. Nos. 5,334,646 and 5,508,334 disclose various SEBS copolymers having jelly-like characteristics, but the polymers described therein are not practical for use as a dental floss due to their undesirable tensile strength at break and elongation at break characteristics. The present inventors discovered that a suitable dental floss could be made by mixing from 1 to 20% by weight of a homopolymer of polypropylene with the SEBS and a plasticizing oil to provide an elastomeric composition that can be elongated up to 1,500% of its initial length without breaking, that has a tensile strength peak at breaking point, for a 2 mm wide sample, as measured on an Instron 4464 with 2.76×10$^5$ Pa (40 psig) grips, of less than 20 N·min, and that has an elongation at breaking point, for a 2 mm wide sample, as measured on an Instron 4464 with 2.76×10$^5$ Pa (40 psig) grips, of more than 100%.

Suitable block copolymers employed have the more general configuration A-B-A wherein each A is a crystalline polymer end block segment of polystyrene; and B is a elastomeric polymer center block segment of poly(ethylene-butylene). These block polymers often are referred to as SEBS block copolymers, and are readily available from a variety of commercially available sources, or can be specially designed using the guidelines provided herein, depending on the desired properties. The poly(ethylene-butylene) and polystyrene portions may be incompatible such that they can form a two-phase system consisting of sub-micron domains of glassy polystyrene interconnected by flexible poly(ethylene-butylene) chains. These domains serve to crosslink and reinforce the structure. This physical elastomeric network structure is reversible, and heating the polymer above the softening point of polystyrene temporarily disrupts the structure, which can be restored by lowering the temperature.

The SEBS block copolymers useful in various embodiments can include a broad range of styrene end block to ethylene/butylene center block ratios of approximately 20:80 or less to 40:60 or higher. Various styrene-ethylene-butylene-styrene block copolymers are commercially available from Shell Chemical Company and Pecten Chemical Company (divisions of Shell Oil Company) under trade designations Kraton G 1651, Kraton G 4600, Kraton G 4609 and the like. Other grades of (SEBS) polymers also can be utilized and include Kraton G 1855X which has a Specific Gravity of 0.92, Brookfield Viscosity of a 25 weight percent solids solution in toluene at 25° C. of 40,000 cps or 8,000 to 20,000 cps at a 20 weight percent solids solution in toluene at 25° C.

The styrene to ethylene and butylene weight ratios can vary anywhere within the following ratios 19:81, 20:80, 21:79, 22:78, 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and the like. Other ratio values of less than 19:81 or higher than 51:49 are also possible.

Other suitable block copolymers useful in various embodiments are those manufactured by Kuraray Co., Ltd., Tokyo, Japan, under the tradename SEPTON™. These block copolymers include, for example, styrene-ethylene/propylene-styrene block polymers (SEPS), styrene-ethylene/butylene-styrene block polymers (SEBS), styrene-ethylene-ethylene/propylene-styrene block polymers (SEEPS), and the like.

The block copolymer (either SEBS or SEPTON) preferably is admixed with from 1% to 20% by weight, more preferably from 3% to 15%, based on the total weight of the elastomeric mixture (including the plasticizer oil), of a polypropylene homopolymer. Polypropylene homopolymers are commercially available from The Dow Chemical Company, (DOW®Polypropylene 5D49, DOW®Polypropylene 5D98, DOW®Polypropylene 5E16S, DOW®Polypropylene 5E89, and the like), DuPont, GE, and others. While not intending on being bound by any theory, the inventors believe that by including a minor amount of the more rigid polypropylene homopolymer into the mixture of the elastomeric copolymer, a more suitable dental floss product can be achieved, having the desired tensile strength and elongation at break suitable for a dental floss product.

Plasticizers suitable for use in practicing are known in the art, they include rubber processing oils such as paraffinic and naphthenic petroleum oils, highly refined aromatic-free paraffinic and naphthenic food and technical grade white petroleum mineral oils, isopropyl myristate, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight. Many such oils are known and commercially available. Examples of representative commercially oils include Amoco® polybutenes, hydrogenated polybutenes and polybutenes with epoxide functionality at one end of the polybutene polymer: Example of such polybutenes include: L-14 (320 Mn), L-50 (420 Mn), L-100 (460 Mn), H-15 (560 Mn), H-25 (610 Mn), H-35 (660 Mn), H-50 (750 Mn), H-100 (920 Mn), H-300 (1290 Mn), L-14E (27-37 cst @ 100° F. Viscosity), L-300E (635-690 cst @ 210° F. Viscosity), Actipol E6 (365 Mn), E16 (973 Mn), E23 (1433 Mn) and the like. Example of various commercially oils include: ARCO Prime and Tufflo oils, other white mineral oils include: Bayol, Bernol, American, Blandol, Drakeol, Ervol, Gloria, Kaydol, Litetek, Marcol, Parol, Peneteck, Primol, Protol, Sontex, and the like.

It is preferred in the various embodiments that the elastomeric copolymer is hydrogenated, and that the mid-block chain (e.g., ethylene/propylene copolymer, etc.) is unsaturated. The elastomeric copolymer, either the SEBS or other SEPTON copolymer comprises from 50% to 99% by weight of the melted blend, more preferably from 70% to 99%, more preferably from 80% to 99%, and most preferably from 85%, 90%, or 95%. The amount of styrene present in the elastomeric copolymer can range from 20% to 40% by weight of styrene, e.g., 35% to 35%, or 30%. It is preferred that the polypropylene homopolymer is included in the blend in an amount of from 1% to 20% by weight, based on the weight of the melted blend, more preferably from 2% to 15%, and most preferably, 5%, 10%, or 15%.

The overall composition, including the blend of polypropylene homopolymer, and elastomeric block copolymer, and the additives, may include the blend in an amount of from 30% to 100% by weight of the blend, from 75% to 99% by weight of the blend, or more than 95% by weight of the blend.

The dental floss compositions may also include one or more flavoring agents. Flavoring agents that may be used include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the gel composition at a concentration of 0.01% to 5% by weight, more preferably from 0.05 to 1.5%, and more preferably, from 0.1% to 1% by weight. The gel compositions may also include one or more colors, e.g., 0.001% to 1%, and more preferably from 0.01% to 0.5% by weight of the overall composition. The elastomeric dental floss therefore may be slightly colored, or may be translucent or transparent, although a colored product is preferred.

The dental floss product described herein may further comprise additional ingredients selected from a fluoride ion source, an abrasive, an antiseptic or antimicrobial agent, an analgesic agent, an anti-inflammatory agent, L-arginine, L-arginine bicarbonate, a coagulant, a vitamin, and a combination of two or more thereof. In some embodiments, the dental floss comprises a fluoride ion source. A wide variety of fluoride ion-yielding materials can be employed as sources of fluoride ions in the present compositions. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof.

In some embodiments, at least one of the one or more particles is an abrasive particle. In some embodiments, the elastomeric dental floss comprises more than one abrasive particle. In some embodiments, the abrasive particles may assist in the removal of debris when the gel is used, e.g., as a dental floss.

In some embodiments, the abrasive particles are embedded in the gel composition of the floss prior to extrusion or injection. In some embodiments, at least one of the one or more particles can be protruded from the floss during use by stretching the floss. In some embodiments, at least one of the one or more particles can be selectively protruded from the floss during use by selectively stretching the floss.

In some embodiments, the abrasive particles are added to the composition in an amount of 0.01-10 wt. %, or 0.1-5 wt. %, or 2.1-10 wt. % or greater than 2 wt. %. In some embodiments, the particles are added to the elastomer prior to extrusion or injection.

Suitable abrasive particles include but are not limited to silica, precipitated calcium carbonate, di-calcium phosphate, mica, crystalline alumino-silicate, precipitated silica, glass beads, glass bubbles, glass microspheres, ceramic microspheres and high melting point polymers (e.g., polymers having a melting point greater than 200° C. or the maximum processing temperature during manufacture of the floss). One or more than one type of abrasive particle can be added to the floss.

The particles preferably range in size from 0.1-700 microns, or 1-500 microns or 2-125 microns or 300-500 microns or greater than 300 microns. In certain embodiments, the abrasive particles have an average diameter of greater than 2 microns. In certain embodiments, the abrasive particles have an average diameter of from about 2 to about 700 microns. In some embodiments, the abrasive particles have an average diameter of from about 25 to about 650 microns. In some embodiments, the abrasive particles have an average diameter of from about 50 to about 600 microns. In some embodiments, the abrasive particles have an average diameter of 75 to about 550 microns. In some embodiments, the abrasive particles have an average diameter of 100 to about 450 microns. In some embodiments, the abrasive particles have an average diameter of from about 200 to 425 microns. In some embodiments, the abrasive particles have an average diameter of from about 225 to about 400 microns. In some embodiments, the abrasive particles have an average diameter of from about 275 to about 375 microns. In some embodiments, the abrasive particles have an average diameter of from about 300 to 350 microns. In some embodiments, the abrasive particles have an average diameter of about 350 microns.

The quantity of particles can be selected to provide a desired effect on the resulting floss. In certain embodiments, a sufficient number of particles is provided such that the floss has a particle density of 0.1-100 or 0.5-50 or 1-25 particles/$mm^3$. In some embodiments, the particle density dictates the number of nodules projecting from the surface of the stretched floss (i.e., the nodule density). In certain embodiments, the stretched nodule density for a floss stretched to twice its relaxed length is 0.1-100 or 0.5-50 or 1-25 nodules/$mm^3$. It should be understood that the nodule density need not be precisely the same value as the particle density due to, e.g., non-protruding particles within the matrix. In certain embodiments, the stretched nodule density for a floss stretched to twice its relaxed length is 1.1× or 1.5× or 2× or 4× or 8× or 10× or 100× or 1000× greater than the relaxed nodule density for the floss in its relaxed state.

The shape of the particles is not particularly limited. The particles may be any of a number of different shapes, such as spherical, square, cylindrical, irregular and the like, the shape being dependent primarily on the particulate manufacturing method employed.

In some embodiments, after adding the particles to the elastomer, the mixture is then formed into a filament with an extrusion or injection process. In some embodiments, the particles are embedded in the elastomer during the forming process. Particles residing in the vicinity of the outer surface of the filament are only partially protruded. In some embodiments, at least one of the one or more particles pierces the elastomeric matrix. In some embodiments, at least one of the one or more particles distends the surface of the elastomeric matrix. In some embodiments, the elastomeric matrix is a thermoplastic elastomer matrix.

When the filament is stretched, its outside diameter is reduced. In some embodiments, the tensile stress affects the physical shape of the elastomeric matrix, but does not affect the physical shape of the particles. In some embodiments, the user can selectively (and reversibly) adjust the abrasiveness of the floss by applying greater tensile stress to the floss such that greater portions of the particles protrude from the floss. The selective exposure of these particles provides and enhances the following attributes and functions of these types of dental floss: (a) abrasiveness; (b) interdental cleaning; (c) removal of dental plaque and extrinsic stains; (d) mouthfeel and sensory effects; (e) gum scrub sensation; (f) sensory cue for cleaning; and (g) improved finger grip. In addition, the appearance of the floss can be selectively altered where the particles are pigmented, dyed or otherwise colored differently than the thermoplastic elastomer of the floss.

It is believed that the aforementioned benefits provided by incorporating the particles into the elastomer prior to extrusion or injection would not be provided by a post-extrusion or post-injection process of applying particles to the floss, such as the process taught in U.S. Pat. No. 5,918,609.

The elastomeric dental floss may also comprise an antiseptic or antimicrobial agent selected from halogenated diphenyl ethers (e.g., triclosan), herbal extracts and essential oils (e.g. rosemary extract, thymol, menthol, eucalyptol, methyl salicylate), bisguanide antiseptics (e.g., chlorhexidine, alexidine or octenidine), quaternary ammonium compounds (e.g., cetylpyridinium chloride (CPC)), phenolic antiseptics, hexetidine, povidone iodine, delmopinol, salifluor, metal ions (e.g., zinc salts, for example, zinc citrate, zinc oxide, zinc lactate, and the like), sanguinarine, propolis, and combinations thereof.

In certain embodiments, the elastomeric dental floss may optionally comprise an analgesic agent, an anti-inflammatory agent, a coagulant, a vitamin, or a combination thereof.

In forming the elastomeric dental floss, the polypropylene and elastomeric copolymer preferably are blended and melted together. A plasticizer preferably is added in an amount sufficient to cause the gel to retain a solid structure, but also be deformable. The mixture then may be extruded or injection molded into sheets or strands and allowed to cool. The extruded sheets and strands may be of any diameter. Preferably, the diameter of the extrusion is such that when the gel is stretched 150% to 1000%, and thus causing the diameter to narrow, the narrowed diameter of the gel composition may easily slide between the teeth. It is preferred that the dental floss have a diameter of from about 0.5 mm to about 10 mm, as measured on a circular cross-section, and more preferably from about 1.0 mm to about 3 mm, and most preferably about 2 mm. It should be noted that the exact diameter of the gel is not important, since the gel will continue to stretch and narrow when applied between the teeth until it reaches a sufficiently narrow diameter that allows for the gel to slide between the teeth.

The elastomeric dental floss also preferably has a basis weight within the range of from 1 to 10 gram/m, and more preferably from 1.5 to 5 g/m, and most preferably from 1.6 to 3.5 g/m. The elastomeric dental floss preferably has an apparent density of from 0.25 to 2.5 g/m, more preferably from 0.5 to 1.5 g/m, and most preferably from 0.75 to 1 g/m. The average diameter of the elastomeric dental floss before breaking preferably ranges from 0.1 to 0.75 mm, more preferably from 0.2 to 0.5 mm, and most preferably from 0.3 to 0.4 mm.

The elastomeric dental floss preferably can be stretched up to 1,500% of its original length without breaking. Using an INSTRON® apparatus, preferably and INSTRON® 4464, commercially available from Instron Corporation, Norwood, Mass., samples of the elastomeric dental floss can be tested for elongation at break and tensile strength peak at the breaking point. Preferably, the Instron apparatus is used with grips capable of holding the sample at or near $2.76 \times 10^5$ Pa (40 psig). The samples of the elastomeric dental floss used in the Instron apparatus may have a thickness of 2 mm, a width of 2 mm at the minimum center notch, with a total width of 10 mm, and a length of 29.5 mm on each side of the notch, and a notch length of 11 mm. Thus, the diameter of the relaxed specimen is 1.9 mm, which is approximately equal to the width and thickness at the center of the notch in the middle of the sample.

Using this testing procedure, the elastomeric dental floss preferably has tensile strength peak at breaking point of less than 22 N·m, more preferably less than 20 N·m, and most preferably less than 18 N·m. The elastomeric dental floss also preferably has an elongation at breaking point, for a 2 mm wide sample (at the center of the notch—i.e., at its thinnest point), of greater than 100%, more preferably greater than 150%, and most preferably greater than 200%.

The elastomeric dental floss compositions also may be coated on to a core to be used as dental floss. The core may be a fiber, which may be a multifilament fiber of polypropylene, nylon, polyester, or other polymers capable of imparting a tensile strength and/or rigidity to the floss, and may be any fiber known by those of skill in the art to be useful for forming a dental floss. Methods of manufacturing such fiber flosses are well known in the art. For example, fiber dental floss may be produced from nylon, as nylon salt is polymerized and the resulting polymer is pumped or extruded to form monofilaments. The filaments are allowed to harden, and then combined to form a strand of floss. Dental floss fibers may be produced from polytetrafluoroethylene (PTFE). In some embodiments, the polymer is melted and extruded into thin strands. In some embodiments, following manufacture of the fiber floss, the fiber floss is passed through the compositions so that the fiber becomes coated. Methods for coating fiber dental floss/core are also known in the art. In some embodiments, the fiber dental floss/core is treated in an emulsion bath comprising the gel compositions. The emulsion bath may optionally contain one or more waxes which adhere to the fiber floss, and thereby cause the gel composition to adhere to the core. In another embodiment, fiber floss comprising a non-PTFE fiber is coated with a first and a second coating overlaying the first coating. The first coating is a nylon bonding coating, and the second coating is a composition.

In providing a multifilament coated core, the composition and number of the filaments must be chosen. The number of filaments will be from 2 to 250 and preferably 2 to 100 depending on the denier of the filaments. The filaments may be twisted with 1 to 5 twists per inch to form the ribbon of floss. The twisting provides integrity of the floss on the spool and during subsequent handling, e.g., coating. Flavors can also be applied as a liquid or a solid. It is preferred to use a spray dried solid. Likewise, the various other additives can be applied as a liquid or a solid. When applied as a liquid the floss is dried prior to being wound onto a spool. The drying can be by radiant drying or air drying. After drying, the floss is wound onto a spool. The fibers may then be removed from the spool and coated with the gel composition.

In another aspect, the core within the gel coated core may have differing or alternative arrangements within the gel; that is to say, the core does not necessarily need to be straight, or taut when coated with the gel composition. Thus, the core may be relaxed, or formed into a "coil" shape when coated with the gel composition. Such an arrangement may be desirable to resist breakage of the dental floss, e.g., to provide two separate breaking points. Thus, for example, a core is arranged in a coil fashion and then coated with the gel composition to form a dental floss. The length of the dental floss is governed by the length of the gel composition, and when used, the gel composition and core will simultaneously elongate. In one embodiment, the tensile strength of the core is greater than the tensile strength of the gel composition, so that if the gel composition fractures under stress, the core remains intact, e.g., to floss between teeth. In another embodiment, the tensile strength of the gel composition is greater than the tensile strength of the core, so that if the core fractures under stress, the gel composition remains intact, e.g., to floss between teeth. In either of the two embodiments, although one component of the floss has broken, the other component remains intact. Such an arrangement may be desirable, as a dental floss which breaks while being used often creates discomfort on the user.

In some embodiments, at least one particle protrudes from the elastomeric dental floss after a tensile force has been applied. In some embodiments, between 1 and 500 particles per square millimeter of surface area protrude after a tensile force has been applied. In some embodiments, between 50 and 250 particles per square millimeter of surface area protrude after a tensile force has been applied.

In some embodiments, at least one of the one or more particles protrudes to the minimal amount observable during use. In some embodiments, at least one of the one or more particles protrudes to the minimal amount perceptible. In some embodiments, at least one of the one or more particles protrudes to greater than 1 micron above the surface of the elastomeric matrix. In some embodiments, at least one of the one or more particles protrudes a distance greater than 1 micron above the surface of the elastomeric matrix. In some embodiments, at least one of the one or more particles protrudes a distance less than 700 microns above the surface of the elastomeric matrix. In some embodiments, at least one of the one or more particles protrudes a distance between 10 and 250 microns above the surface of the elastomeric matrix.

Some embodiments provide a dental floss comprising: an elastomeric matrix; and a plurality of particles incorporated in the matrix, wherein at least one of the particles protrude from the outer surface of the matrix during use. Other embodiments provide a dental floss wherein the elastomer matrix comprises a blend of an elastomeric block copolymer and polypropylene; and a plasticizer.

The processing conditions used to manufacture the elastomeric dental floss of the preferred embodiments will vary depending on the final properties. Preferably, a multizone single-screw extruder is used. The screw diameter can vary depending on the scale of product manufactured, from anywhere from 25-30 mm for lab scale, to much larger for commercial scale applications. Those having ordinary skill in the art are capable of designing a suitable extruder to manufacture the elastomeric dental floss compositions using the guidelines provided herein. A coextrusion process having a multiple layers could also be used to produce the dental floss.

In some embodiments, the dental floss compositions described herein can be used to treat or prevent a disease or condition of the oral cavity. In some embodiments, the disease or condition of the oral cavity is gingivitis or periodontitis.

Alternatively, the elastomeric dental floss products can be manufactured using an injection molding technique. Again, those having ordinary skill in the art will be capable of designing a suitable injection molding method and apparatus, using the guidelines provided herein.

The preferred embodiments now will be described in more detail with reference to the following non-limiting examples.

EXAMPLES

Example 1

The inventive elastomeric dental floss was prepared by melt extrusion in a multizone single screw MIOTTO® extruder, (Miotto Ltda, Sao Paulo, Brazil), having a screw diameter of 30 mm, an L/D ratio of 25, a compression rate of ⅓, a nominal capacity of 60 kg/hr, and a material flow rate of 12 m/sec. The extruder body temperatures at the various zones were (Z1=164° C.; Z2=164° C.; Z3=173; and Z4=172° C.), and the extruder head temperatures at the various zones were (Z1=175° C.; and Z2=175° C.). The product was cooled in a water cooling tank maintained at 28° C.

The elastomeric dental floss was prepared by admixing in the extruder 100% by weight, based on the total weight of the dental floss, of a polymer blend of SEBS (styrene-ethylene/propylene-styrene) block copolymer 25.8%, a propylene homopolymer 19.396%, a naphthenic mineral oil 51.7%, 0.1% of antioxidant/stabilizer component, 0.02% by weight of a colorant, and 3% by weight of mint flavoring. The elastomeric dental floss had a diameter of 1.9 mm, a basis weight of 2.45 g/m, and an apparent density of 0.83 g/m. Prior to extrusion, amorphous silica particles were added to the composition in the extruder in an amount of about 1-2% based on the weight of the composition. The particles had a nominal size of about 350 microns (prior to mixing, which could conceivably cause a particle size reduction). Filaments were extruded with a round shape having an outside diameter of about 1.8 mm. Filaments obtained in this example are shown in FIGS. 1 and 2.

FIG. 1 depicts a filament 10 in its relaxed state, wherein little if any tensile stress is being applied thereto.

Figure 2:
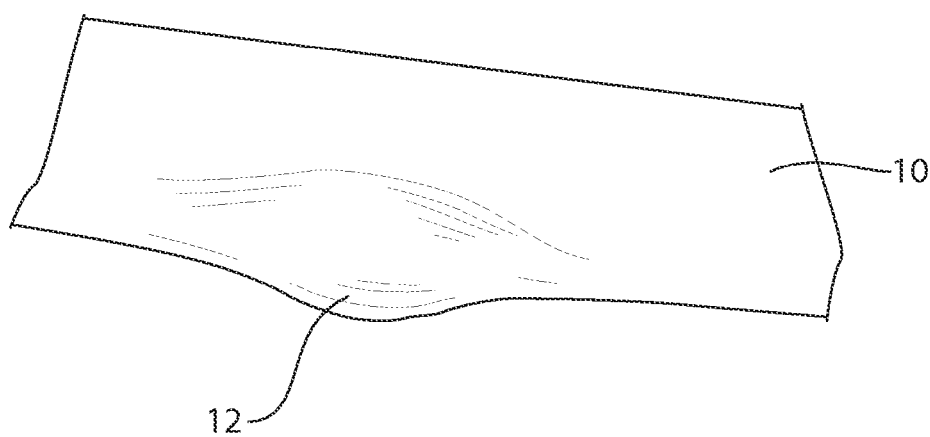
FIG. 2 depicts an embodiment of the inventive floss containing amorphous silica particles.

FIG. 2 depicts a filament 10 stretched by hand such that its outside diameter (as measured from opposing thermoplastic elastomer surfaces) was reduced to about 0.7-0.9 mm. Nodule 12 comprising a partially protruded silica particle is apparent only in FIG. 2.

The invention has been described above with reference to illustrative examples, but it is to be understood that the invention is not limited to the disclosed embodiments. Alterations and modifications that would occur to one of skill in the art upon reading the specification are also within the scope of the invention, which is defined in the appended claims.

What is claimed is:

1. A dental floss comprising:

an elastomeric matrix containing one or more particles;

wherein the dental floss is adapted such that at least one of the one or more particles protrudes from the matrix in increasing amounts as increasing tensile stress is applied to the dental floss, wherein the elastomeric matrix comprises:

a blend of an elastomeric block copolymer and polypropylene; and a plasticizer, and wherein at least one of said one or more particles is an abrasive particle, and the dental floss comprises from 0.1 to 5% by weight based on a weight of the dental floss, of abrasive particles, wherein the abrasive particles comprise at least one member selected from the group consisting of silica, precipitated calcium carbonate, di-calcium phosphate, mica, crystalline alumino-silicate, precipitated silica, glass beads, glass bubbles, glass microspheres, ceramic microspheres and polymers having a melting point above 200° C.;

wherein the elastomeric block copolymer comprises a styrene-ethylene/butylene-styrene block copolymer and comprises 50% to 99% by weight of the blend.

2. The dental floss of claim 1, wherein the dental floss is provided by a process wherein the elastomeric block copolymer, the polypropylene, the plasticizer and the one or more particles are mixed and subsequently extruded or injected.

3. The dental floss of claim 1, wherein the polypropylene comprises 1% to 50% by weight of the blend.

4. The dental floss of claim 1, wherein the blend comprises 30% to 99% by weight of the dental floss.

5. The dental floss of claim 1, wherein the styrene-ethylene/butylene-styrene block copolymer comprises 20% to 40% by weight of styrene.

6. The dental floss of claim 1, wherein the plasticizer is a mineral oil, naphthenic oil, or a combination thereof.

7. The dental floss of claim 1, further comprising a flavorant, a colorant, a fluoride ion source, an antiseptic or antimicrobial agent, an analgesic agent, an anti-inflammatory agent, a coagulant, a vitamin, or a combination of two or more thereof.

8. The dental floss of claim 1, wherein the dental floss is adapted to withstand being elongated up to 1500% of an initial length without breaking.

9. The dental floss of claim 8, having a tensile strength peak at breaking point, for a 2 mm wide sample, as measured on an Instron 4464 with $2.76 \times 10^5$ Pa (40 psig) grips, of less than 18 $Nm^{-2}$, and having an elongation at breaking point, for a 2 mm wide sample, as measured on an Instron 4464 with $2.76 \times 10^5$ Pa (40 psig) grips, of more than 200%.

10. The dental floss of claim 1, having a tensile strength peak at breaking point, for a 2 mm wide sample, as measured on an Instron 4464 with $2.76 \times 10^5$ Pa (40 psig) grips, of less than 20 $Nm^{-2}$.

11. The dental floss of claim 1, having an elongation at breaking point, for a 2 mm wide sample, as measured on an Instron 4464 with $2.76 \times 10^5$ Pa (40 psig) grips, of more than 100%.

12. The dental floss of claim 1, having a maximum elongation before breaking, for a 2 mm wide sample, as measured on an Instron 4464 with $2.76 \times 10^5$ Pa (40 psig) grips, of less than 0.35 mm.

13. The dental floss of claim 1, wherein the abrasive particles have an average diameter of from 2 to 125 microns.

14. The dental floss of claim 1, wherein the floss has a particle density of 0.1-100 particles/mm$^3$.

15. The dental floss of claim 1, wherein a stretched nodule density for the dental floss stretched to twice a relaxed length is 0.1-100 particles/mm$^3$.

16. The dental floss of claim 1, wherein a stretched nodule density for the dental floss stretched to twice a relaxed length is at least 1.1× greater than a relaxed nodule density for the dental floss at the relaxed length.

17. The dental floss of claim 1, having a tensile strength peak at breaking point, for a 2 mm wide sample, as measured on an Instron 4464 with 2.76×10$^5$ Pa (40 psig) grips, of less than 18 Nm$^{-2}$.

18. The dental floss of claim 1, having an elongation at breaking point, for a 2 mm wide sample, as measured on an Instron 4464 with 2.76×10$^5$ Pa (40 psig) grips, of more than 200%.

19. A dental floss comprising:
an elastomeric matrix; and
a plurality of particles incorporated in the matrix, wherein at least one of the particles protrude from the outer surface of the matrix during use, wherein the elastomeric matrix comprises:
(a) a blend of an elastomeric block copolymer and polypropylene; and
(b) a plasticizer,
and wherein at least one of the particles is an abrasive particle, and the dental floss comprises from 0.1 to 5% by weight based on a weight of the dental floss, of abrasive particles, wherein the abrasive particles comprise at least one member selected from the group consisting of silica, precipitated calcium carbonate, di-calcium phosphate, mica, crystalline alumino-silicate, precipitated silica, glass beads, glass bubbles, glass microspheres, ceramic microspheres and polymers having a melting point above 200° C.

* * * * *